United States Patent
Schulz

(10) Patent No.: US 7,383,738 B2
(45) Date of Patent: Jun. 10, 2008

(54) METHOD TO EXTEND TESTING THROUGH INTEGRATION OF MEASURED RESPONSES VIRTUAL MODELS

(75) Inventor: Bradley D. Schulz, Savage, MN (US)

(73) Assignee: MTS Systems Corporation, Eden Prairie, MN (US)

( * ) Notice: Subject to any disclaimer, the term of this patent is extended or adjusted under 35 U.S.C. 154(b) by 0 days.

(21) Appl. No.: 11/004,308

(22) Filed: Dec. 3, 2004

(65) Prior Publication Data

US 2005/0120802 A1     Jun. 9, 2005

Related U.S. Application Data

(60) Provisional application No. 60/527,232, filed on Dec. 5, 2003.

(51) Int. Cl.
*G01B 7/16* (2006.01)
(52) U.S. Cl. ........................................ 73/781
(58) Field of Classification Search ............... 73/781; 623/912
See application file for complete search history.

(56) References Cited

U.S. PATENT DOCUMENTS

| | | | |
|---|---|---|---|
| 3,597,967 A | 8/1971 | Drexler et al. ................. 73/91 |
| 4,882,677 A | 11/1989 | Curran .................. 364/413.02 |
| 5,014,719 A | 5/1991 | McLeod ..................... 128/774 |
| 5,259,249 A | 11/1993 | Fetto ........................... 73/794 |
| 5,511,431 A | 4/1996 | Hinton ........................ 73/806 |
| 5,936,858 A * | 8/1999 | Arai ............................ 700/30 |
| 5,937,530 A | 8/1999 | Masson ....................... 33/534 |
| 5,952,582 A * | 9/1999 | Akita et al. .................... 73/855 |
| 5,959,215 A | 9/1999 | Ono et al. .................... 73/798 |
| 5,999,168 A * | 12/1999 | Rosenberg et al. ......... 345/161 |
| 6,171,812 B1 | 1/2001 | Smith et al. ............. 435/40.52 |
| 6,418,392 B1 | 7/2002 | Rust et al. ................... 702/123 |
| 6,502,837 B1 | 1/2003 | Hamilton et al. ........ 280/5.515 |
| 6,510,740 B1 * | 1/2003 | Behm et al. .................. 73/708 |
| 6,538,215 B2 | 3/2003 | Montagnino et al. .... 177/25.16 |
| 6,571,373 B1 | 5/2003 | Devins et al. ................. 716/5 |
| 6,581,437 B2 | 6/2003 | Chrystall et al. ................ 73/7 |
| 6,715,336 B1 * | 4/2004 | Xu .................................. 73/7 |

(Continued)

FOREIGN PATENT DOCUMENTS

DE     27 28 007     6/1977

(Continued)

OTHER PUBLICATIONS

The858 Mini Bionix II Test System Brochure; mts.com/downloads/300213-01.pdf; pub. 1999.*

(Continued)

*Primary Examiner*—Max Noori
(74) *Attorney, Agent, or Firm*—Steven M. Koehler; Westman, Champlin & Kelly P.A.

(57) ABSTRACT

A system and method to expand capabilities of simulation and durability testing of a specimen under test utilizing a virtual signal that is generated by combining the actual measured signal from a transducer with a supplemental or simulated signal created by a function based on position, load or another known or measurable parameter. This virtual signal may then be inserted into a control loop to adapt the system to this new, calculated or combined signal.

21 Claims, 2 Drawing Sheets

U.S. PATENT DOCUMENTS

| | | |
|---|---|---|
| 6,721,922 B1 | 4/2004 | Walters et al. .................. 716/1 |
| 2001/0045941 A1* | 11/2001 | Rosenberg et al. ......... 345/161 |
| 2002/0029610 A1 | 3/2002 | Chrystall et al. ................. 73/7 |
| 2002/0170361 A1* | 11/2002 | Vilendrer et al. ............. 73/849 |
| 2003/0029247 A1 | 2/2003 | Biedermann et al. ......... 73/768 |
| 2004/0019382 A1 | 1/2004 | Amirouche et al. ..... 623/18.11 |
| 2004/0019384 A1 | 1/2004 | Kirking et al. .......... 623/20.14 |

FOREIGN PATENT DOCUMENTS

| | | |
|---|---|---|
| DE | 44 11 508 A1 | 2/1994 |
| EP | 0 919 201 A1 | 9/1998 |

OTHER PUBLICATIONS

PCT International Search Report and Written Opinion of the International Searching Authority, PCT/US2004/040798 dated Jun. 4, 2005.

D.W. Clarke, Adaptive control of a materials-testing machine, 1996, The Institution of Electrical Engineers, pp. 4/1-4/4.

* cited by examiner

METHOD TO EXTEND TESTING THROUGH INTEGRATION OF MEASURED RESPONSES VIRTUAL MODELS

CROSS-REFERENCE TO RELATED APPLICATION

This application claims the benefit of U.S. Provisional Application 60/527,232 filed Dec. 5, 2003.

BACKGROUND OF THE INVENTION

The present invention relates generally to durability testing of test specimens such as but not limited to, artificial orthopedic implants (e.g. hip, knee, spine, etc.). More specifically, the present invention pertains to a system and method for combining measured signals with virtual signals generated by a model to extend the range of mechanical methods of load testing.

Laboratory simulation is a technique that is often used to validate the durability of orthopedic implant designs and to verify manufacturing quality assurance. In the case of the artificial knee joint, it is desirable to place the Anterior-Posterior and Tibial-Rotation degrees of freedom in load or torque control, while at the same time controlling the load in the vertical degree of freedom. Pure displacement control in these directions is deficient because it does not account for the changes in specimens over time or variation between specimen designs (e.g. levels of constraint). In addition, pure load control is made difficult by the variation in constraint levels between specimens and within a given specimen over its operating range (e.g. transitions from static to kinetic friction states, collision with hard mechanical limits built into the specimen, etc.). Previous research exists for the force inputs into the body, relative displacements expected in a healthy joint and the behavior of the surrounding soft tissue. It is also known that over time, as specimens wear, constraint levels and coefficients of friction change. It is not feasible to do long-term durability tests that incorporate all aspects of the in-vivo environment, such as, the living soft tissue. Therefore, commonly utilized test systems face an increasingly difficult task of applying forces to specimens that adequately emulate realistic conditions in addition to compensation techniques in the event of partial failure of the specimen. Design of simulators to apply varying loads is complicated by cross talk between channels and the continuously varying nature of each programmed load. Further difficulties arise from the large variation in implant design and the associated widely varying degrees of joint constraint.

Once an artificial joint is implanted, it is constrained by a combination of mechanical interlock, frictional forces and the soft tissue surrounding the joint. The mechanical interlock and frictional forces may be directly replicated in the specimen, whereas the soft tissue is more difficult to simulate.

Soft tissue reaction forces have been implemented in orthopedic simulators in the past by use of mechanical springs which have significant disadvantages including limited durability, difficulty in changing values, limited mathematical nature of the reaction forces, difficulty in attaining appropriate configuration and overall complexity of the machine.

Therefore, there is a significant need to improve systems that are used to test specimens for durability and other factors. A system that addresses one or more of the shortcomings discussed above would be particularly useful.

SUMMARY OF THE INVENTION

The invention provides a system and method to expand capabilities of simulation and durability testing of test specimens such as those exhibiting soft tissue behavior.

According to one embodiment of the present invention, a virtual signal is generated by combining the actual measured signal from a transducer with a supplemental or simulated signal created by a function based on position, load or another known or measurable parameter. This virtual signal may then be inserted into the control loop to adapt the system to this new, calculated or combined signal.

In another embodiment, multiple virtual parameter thresholds can be used in the control loop described above such that when the threshold of one or more functions is met or exceeded, further actions may be enabled and subsequent functions may be implemented to further the testing.

DETAILED DESCRIPTION OF THE PREFERRED EMBODIMENTS

This invention replaces the solely mechanical methods commonly used with software and hardware by incorporating a virtual model into the control loop and then controlling to this new, calculated virtual load and/or displacement. The virtual load and/or displacement signal is generated by a combination of the actual measured force from a transducer and a supplemental or simulated signal created by a mathematical or other derivable function based on known or measurable parameters (e.g. displacement, temperature, etc.), which exemplified below using "loads" can be represented as:

$$\text{Virtual Load} = \text{Measured Load} + F(n)$$

where $F(n)$ can take any one or a combination of forms including mathematical equations, systems of analog, digital or logical operators, systems of linear or non-linear equations, look-up tables, static and dynamic system models, fuzzy logic, etc., while n can be any known or measurable factor (displacement, temperature, load, etc.).

A similar equation can be provided for systems operating under displacement control:

$$\text{Virtual Displacement} = \text{Measured Displacement} + F(n)$$

This simulation function can be simply calculated real-time through the use of calculated control or expanded through the use of analog, digital or logical operators (such as 'and', 'or', etc.), systems of linear or non-linear equations, look-up tables, static and dynamic system models, fuzzy logic, etc. For example, within a certain range function $F(n)$ could be active, and if the resulting external influences cause a displacement, load or other parameter outside of that range, function $F(n_x)$ could be engaged.

Figure 1:
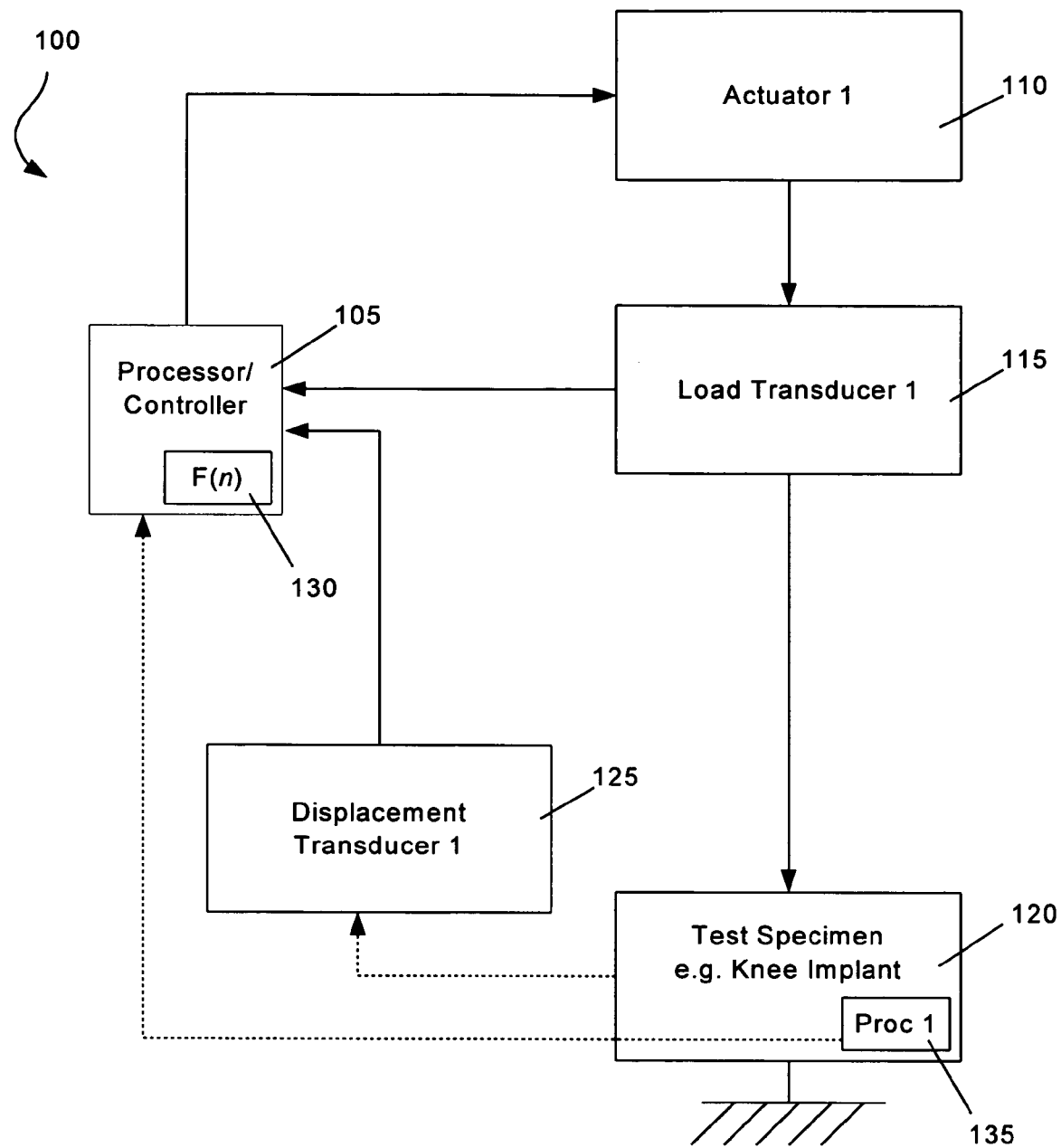
FIG. 1 is a schematic diagram of a system for implementing a simplified embodiment of the present invention.

FIG. 1 illustrates schematically the components of a system 100 for implementing aspects of the present invention described above. System 100 includes an actuator 110 for imparting loads and/or causing displacement of elements of a test specimen 120 such as an artificial knee. Actuator 110 may be a hydraulic, pneumatic, electromechanical device or combination thereof. As appreciated by those skilled in the art, depending on the application, the actuator(s) need support components such as servo-valves, accumulators, power sources, etc. as part of the system 100 but such components are not depicted here since such components are well known.

A processor/controller 105 provides drive signals to the actuator 110 using load control or displacement control techniques. Processor/controller 105 may consist of analog and/or digital electronic configurations, with or without suitable software routines. The load transducer 115 and/or a position or displacement transducer 125 are operatively coupled to the test specimen 120 so as to sense loads and/or displacements in one or more degrees of freedom. The processor/controller 105 receives signals indicative of sensed loads or sensed displacements.

As indicated above, the processor/controller 105 includes a mathematical model or representation 130 of simulated aspects of the test specimen 120 which herein represented as F(n), as described above. The processor/controller 105 receives the actual measured loads and/or displacements from the load transducer 115 and the displacement transducer 125 and combines this information with simulated information in the model F(n) 130. The actuator 110 is controlled by the processor/controller 105 as if the virtual (measured+simulated) loading and/or displacement had actually occurred. Thus, the actuator 110 can be appropriately controlled for repeated cycles wherein after, for example, a durability test, the test specimen 120 can be removed and wear characteristics measured.

In a particularly useful application, system 100 can be used for testing of an artificial knee or other prosthetic/Orthopedic implant. For example, assume it is desired to simulate the sliding between the two major components of the knee during articulation. Although from prior testing, a researcher may know the force input acting on the joint, for example, in a shearing direction, Anterior-Posterior, as well as the displacement of such components, aspects relative to the joint when soft tissues are present can complicate testing. Some approaches have included simulating soft tissue by mechanically applying springs between the two components. However, difficulties using this approach include choosing the right spring, locating it correctly, etc. Furthermore, proper modeling of soft tissue may not be accurate using a mechanical spring. For instance, characteristics of soft tissue may change with time, and thus, for testing an artificial knee, one may like to apply a test that takes the changes of soft tissue over time (aging, healing, etc.) into account as well as historical data from past test results. In addition, the mathematical function allows for the simulation of rate sensitive behavior (visco-elasticity) and insertion of specimen integrated microprocessor hardware into the test control loop. The representation 130 can advantageously include this information. Thus, an aspect of the present invention includes modeling or simulating a mechanical or other system such as the soft tissue as F(n) 130 (e.g. in software), and using this representation as discussed above to control the actuator 110 as a function of the virtual (measured+simulated) loads and/or displacements. In addition, F(n) can account for widely varying degrees of constraint and thereby widely varying specimen design.

In a further embodiment, the test specimen, such as an orthopedic or prosthetic implant, may include a microprocessor 135 and internal sensors for measuring force or other parameters, or detecting limits thereof, etc. An information signal from the microprocessor 135 can be used to control or change the control loop via the F(n) function.

Figure 2:
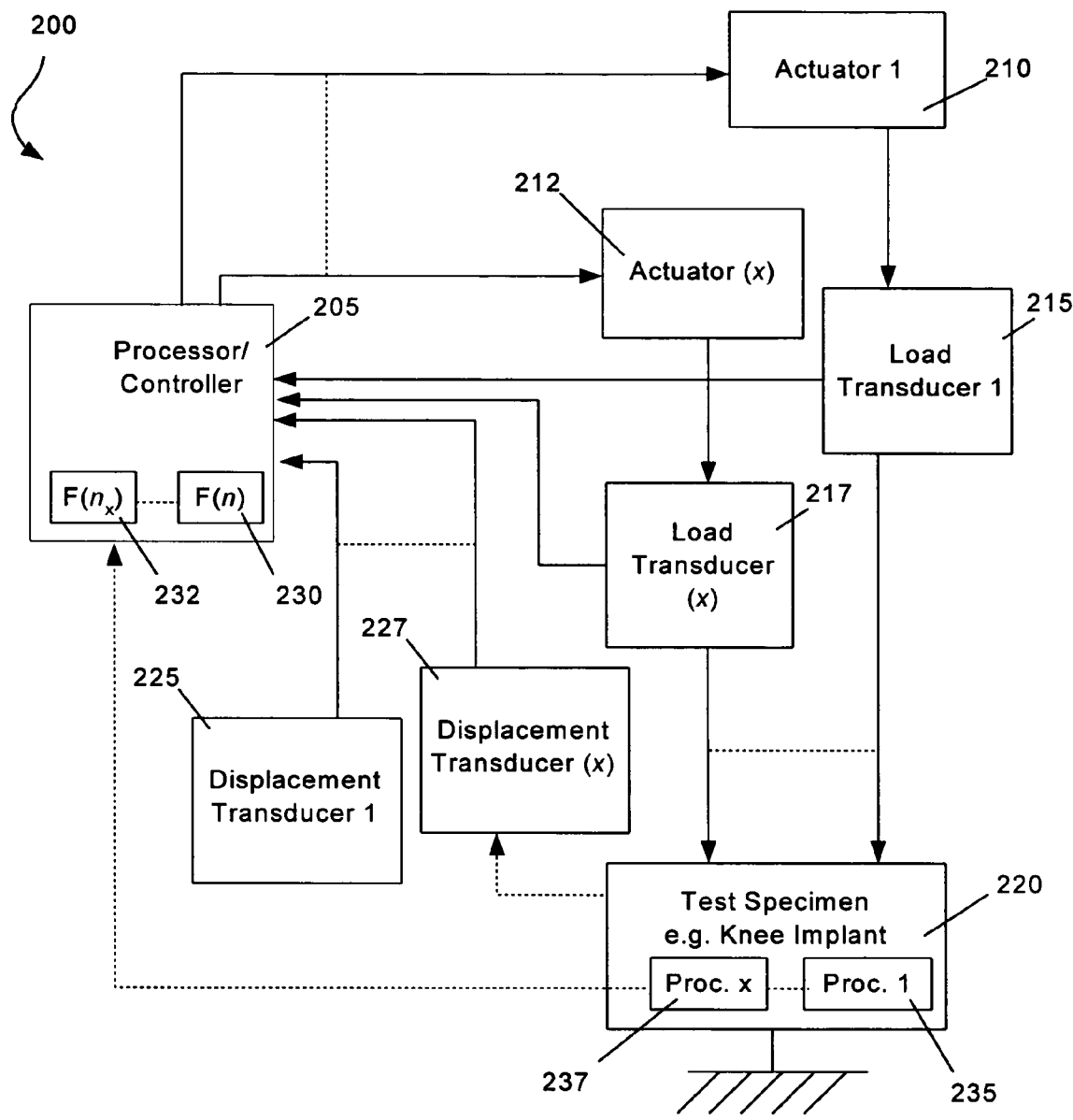
FIG. 2 is schematic diagram illustrating a means for implementing multiple virtual models with various parameters of a more complex test system than that of FIG. 1.

FIG. 2 illustrates another exemplary application similar to FIG. 1 in which a system 200 includes multiple actuators 210 and 212 for imparting loads and/or causing displacement of elements of a test specimen 220 such as an industrial component. A processor/controller 205 provides drive signals to multiple actuators, such as actuators 210 and 212, using load control or displacement control techniques. Load transducer 215 and 217 and position or displacement transducers 225 and 227 are operatively coupled to the test specimen 220 so as to sense loads or displacements in multiple degrees of freedom. The processor/controller 205 receives signals indicative of sensed loads and sensed displacements, while monitoring the result of multiple predetermined models, F(n) 230 and F($n_x$) 232. Signals from multiple load transducers 215 and 217 are combined with multiple displacement transducers 225 and 227 along with simulated information in models 230 and 232, until a threshold is either achieved or exceeded, causing one or more of the actuators 210 and 212 to change its parameter, become activated or disabled from the system 200. In one aspect of such an embodiment, control logic may implement extended measurement capability on the same sample as its properties change over time or begin to degrade under extreme conditions.

In a further embodiment, the test specimen, such as a prosthetic implant, may include multiple microprocessors 235 and 237, and internal sensors for measuring force or other parameters, or detecting limits thereof, etc. An information signal from the multiple microprocessors 235 and 237 can be used to control or change the control loop via the F(n) and F($n_x$) functions.

Although the present invention has been described with reference to preferred embodiments, workers skilled in the art will recognize that changes may be made in form and detail without departing from the spirit and scope of the invention.

What is claimed is:

1. A system for applying loads to a test specimen, the system comprising:
    a controller;
    an actuator operatively coupled to the controller to operate based on control signals therefrom and adapted to apply loads or control displacement of a test specimen;
    one or more transducers that provide signals to the controller indicative of at least one of measured loads or measured displacements on the test specimen; and
    wherein the controller is adapted to control said actuator based on signals from at least one of the one or more transducers and a predetermined representation of additional aspects of the test specimen for generating at least one of a simulated load or a simulated displacement.

2. The system of claim 1 wherein the controller controls the actuator based on input from at least one of the one or more transducers within a predetermined linear operable range.

3. The system of claim 1 wherein the controller includes a representation of additional aspects of the test specimen according to historical measurement data.

4. The system of claim 1 wherein the representation of the controller further comprises multiple parameters whereby more than one actuator may be controlled by the controller based on a single representation.

5. The system of claim 1 wherein the controller comprises more than one representation.

6. The system of claim 5 wherein the stored representations representation of additional aspects of the test specimen further comprise comprises logical operators in order to engage additional representations.

7. The system of claim 6 wherein the engaging of additional representations by use of logical operators allow uninterrupted test of the test specimen.

8. A method for applying loads to a test specimen, the method comprising:
making one or more measurements on a test specimen of at least one of one or more loads or one or more displacements;
controlling an actuator coupled to the test specimen to apply at least one of one or more loads or one or more displacements on the test specimen by combining information indicative of the measurements with corresponding simulated information representative of additional aspects of the test specimen, to produce virtual representations of additional aspects of at least one of loads or displacements that are used to control the actuator.

9. The method of claim 8 wherein controlling by combining information indicative of the measurements with simulated information includes parameters determined through historical data.

10. The method of claim 8 wherein the simulated information includes more than one function.

11. The method of claim 10 wherein the functions further comprise logical operators in order to engage additional functions.

12. The method of claim 11 wherein the additional functions are engaged so as to allow uninterrupted test of the specimen.

13. The method of claim 11 wherein the test specimen is an orthopedic test specimen.

14. An orthopedic test system for applying loads to a test specimen, the system comprising:
a controller;
an actuator operatively coupled to the controller to operate based on control signals therefrom and adapted to apply loads or control displacement of an orthopedic test specimen;
one or more transducers, selected from among one or more load transducers and one or more displacement transducers, wherein the transducers provide signals to the controller indicative of measured loads or displacements on the orthopedic test specimen; and
wherein the controller is adapted to control said actuator based on signals from at least one of the one or more transducers and a representation of additional aspects of the orthopedic test specimen for generating simulated loads and/or displacements.

15. The orthopedic test system of claim 14 wherein the controller controls the actuator based on input from at least one of the one or more transducers within a predetermined linear operable range.

16. The orthopedic test system of claim 14 wherein the controller includes a representation of additional aspects of the orthopedic test specimen according to historical measurement data.

17. The orthopedic test system of claim 14 wherein the representation of the controller further comprises multiple parameters whereby more than one of the one or more transducers may be controlled by the controller based on a single representation.

18. The orthopedic test system of claim 14 wherein the controller comprises more than one representation.

19. The orthopedic test system of claim 18 wherein the representations further comprise logical operators in order to engage additional representations.

20. The orthopedic test system of claim 19 wherein the engaging of additional representations by use of logical operators allow uninterrupted test of the orthopedic test specimen.

21. The system of claim 1, wherein the test specimen comprises one or more processors and one or more internal sensors.

* * * * *